United States Patent
Åström et al.

(10) Patent No.: US 7,085,600 B2
(45) Date of Patent: Aug. 1, 2006

(54) CARDIAC EVENT DETECTOR

(75) Inventors: Magnus Åström, Lund (SE); Leif Sörnmo, Lund (SE); Salvador Olmos, Zaragoza (ES)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 10/493,272

(22) PCT Filed: Sep. 18, 2002

(86) PCT No.: PCT/SE02/01654

§ 371 (c)(1),
(2), (4) Date: Nov. 4, 2004

(87) PCT Pub. No.: WO03/034917

PCT Pub. Date: May 1, 2003

(65) Prior Publication Data

US 2005/0119579 A1 Jun. 2, 2005

(30) Foreign Application Priority Data

Oct. 23, 2001 (SE) .................................. 0103562

(51) Int. Cl.
*A61B 5/04* (2006.01)

(52) U.S. Cl. ........................................ 600/509; 607/27

(58) Field of Classification Search ................. 600/509, 600/513; 607/27
See application file for complete search history.

(56) References Cited

U.S. PATENT DOCUMENTS

| 5,117,833 | A | * | 6/1992 | Albert et al. ................ 600/515 |
| 5,683,425 | A | | 11/1997 | Hauptmann |
| 5,947,909 | A | | 9/1999 | Watrous |
| 6,275,734 | B1 | * | 8/2001 | McClure et al. .............. 607/27 |

FOREIGN PATENT DOCUMENTS

WO    WO 00/72916    12/2000

OTHER PUBLICATIONS

"Interference in Pacemakers," Irnish, PACE, vol. 7, Nov.-Dec. 1994, Part I, pp. 1021-1048.

"Muscle Noise and Interference Behavior in Pacemakers: A Comparative Study," Irnich, PACE, vol. 10, Jan.-Feb. 1987, Part I, pp. 125-132.

"Software QRS Detection in Ambulatory Monitoring—A Review," Pahlm et al. Med. Biol. Eng. Comput., vol. 22 (1984) pp. 289-287.

* cited by examiner

*Primary Examiner*—George Manuel
*Assistant Examiner*—Lenwood Faulcon, Jr.
(74) *Attorney, Agent, or Firm*—Schiff Hardin LLP

(57) ABSTRACT

A detector for detecting a cardiac event in an IEGM has a bank of digital filters composed of at least two filters with substantially different impulse responses corresponding to different properties of the cardiac event. The filters respectively filter different portions of the IEGM and respectively emit a value per time unit corresponding to the morphological resemblance between the IEGM and the finite impulse response. An analyzing unit combines these output values from the filters in a predetermined manner for comparison with predetermined detection criteria.

23 Claims, 8 Drawing Sheets

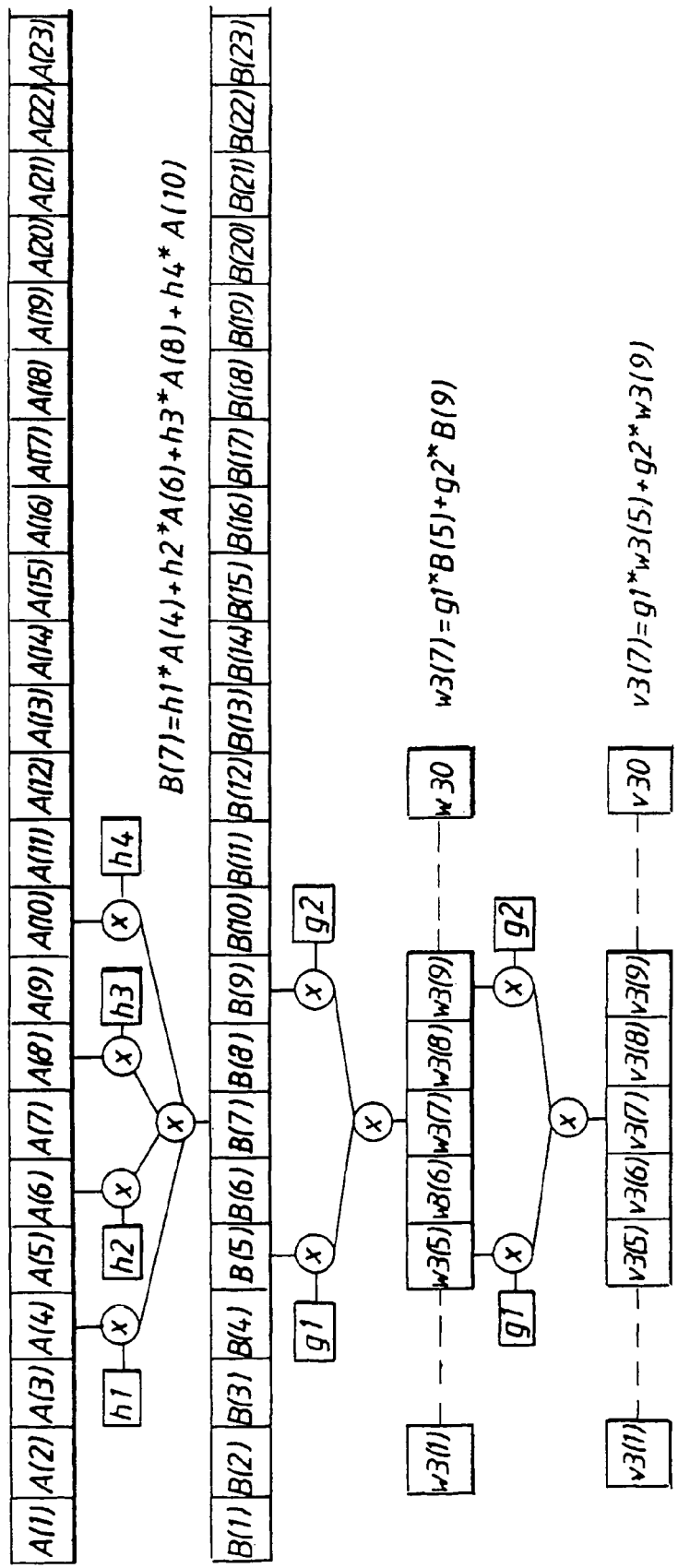

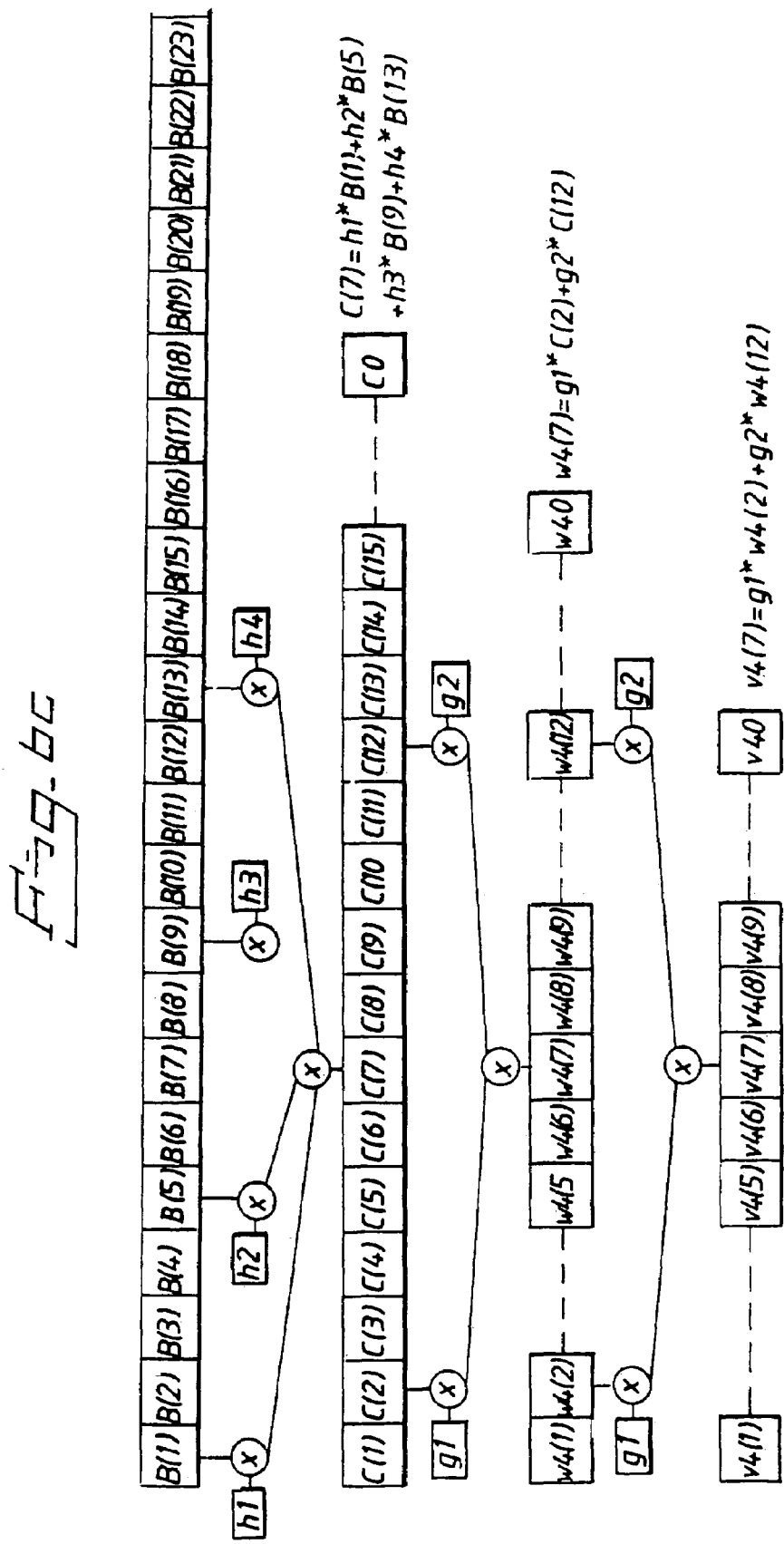

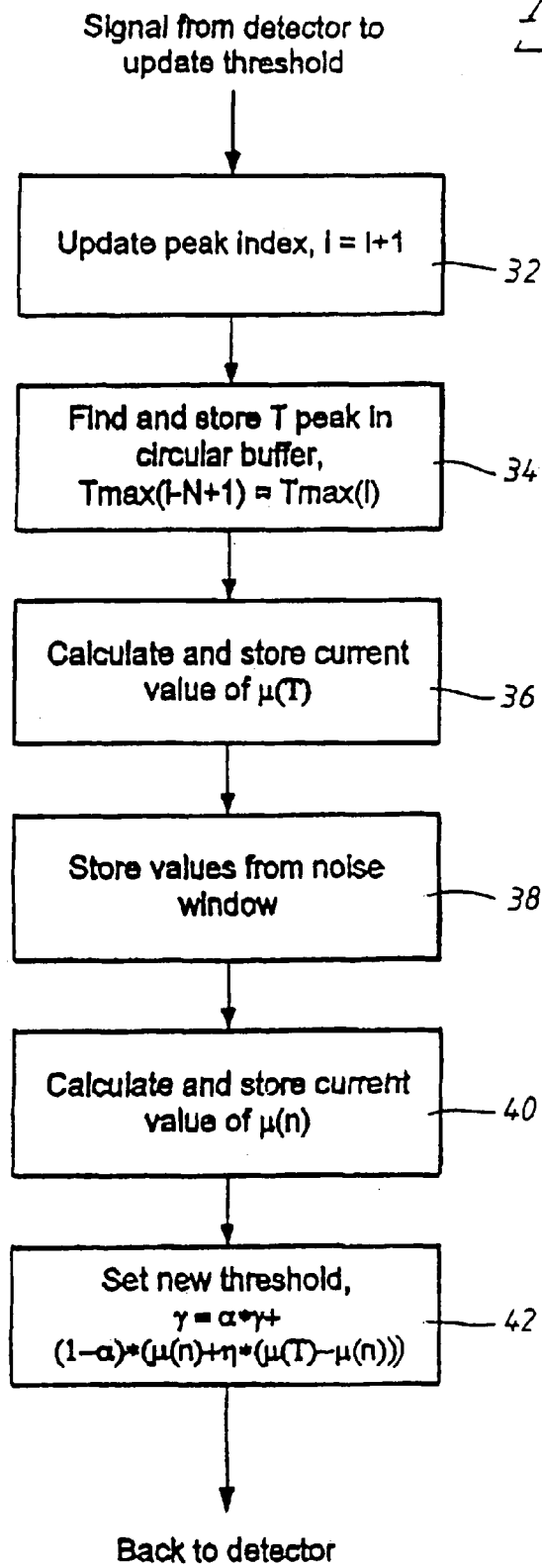

CARDIAC EVENT DETECTOR

BACKGROUND OF THE INVENTION

1. Field of the Invention

The present invention relates to a detector for detecting a cardiac event in an IEGM using a bank of digital filters.

2. Description of the Prior Art

Reliable cardiac event detection is of fundamental importance for the control of implantable heart stimulators, such as pacemakers and defibrillators. An increasing problem in today's society in this connection is the amount of noise sources which to various degree interfere with implantable devices, see e.g. W. IRNICH, "Interference in Pacemakers", PACE, vol. 7, pp. 1021–1048, November–December 1984. During the last decades an increasing number of different types of electrical equipment has been introduced to the general public, which may be potential threats to the correct function of implantable devices. Moreover, internal muscle noise interferes with pacemakers, see W. Irnich "Muscle Noise and Inference Behaviour in Pacemakers: A Comparative Study", PACE, vol. 10, pp. 125–132, January–February 1987.

During the last twenty years a large number of surface electrocardiogram ECG based QRS detectors have been presented for processing surface ECG:s. Many of these QRS detectors exhibit the same basic structure, viz. linear filtering and a non-linear transformation of the signal for the subsequent decision rule, see e.g. O. Pahlm and L. Sörnmo, "Software QRS detection in ambulatory monitoring—a review", Med. Biol. Eng. Comput., vol 22, pp. 289–297, 1984. QRS detectors implemented in implantable medical devices exhibit a similar structure but typically involve only a bandpass filter and an amplitude threshold. However, cardiac event detection using intracardiac electrograms IEGM introduces new demands disqualifying most ECG based QRS detectors. In an implantable heart stimulator the detection decision must be made in real time with a delay of no more than approximately 40 ms. Furthermore, implementation for implantable medical devices introduces power constraints, which in general make use of ECG based QRS detectors impossible. The evolution of digital integrated circuits has allowed for more complex digital detectors and more advanced implantable medical devices. The use of digital detectors also has the advantage of simplifying the implantation of other desirable features such as morphology classification and data compression for post analysis. PCT Application WO 0072916 describes an implantable stimulator that subjects cardiac signals to different filtering. The signals from the different filters are then combined and compared with predetermined criteria to determine if the sought cardiac signal is present or not.

Heretofore, however, digital application specific integrated circuits have been a non-realistic alternative for cardiac event detection in implantable medical devices because of the power demands. There is thus a need for better possibilities to detect cardiac events in implantable medical devices.

SUMMARY OF THE INVENTION

An object of the present invention is to provide an improved detector for detecting cardiac events in IEGM:s that does not exhibit the disadvantages described above.

??This purpose is obtained by a detector of the kind mentioned in the introductory portion and having the characterizing features of claim 1.

The above object is achieved in accordance with the principles of the present invention in a cardiac event detector for detecting a cardiac event in an IEGM, the cardiac event detector having a bank of digital filters respectively having different filter characteristics and an analyzing unit for combining the signals from the filters in a predetermined manner for comparison with defined detection criteria, wherein the filter bank includes at least two filters with substantially orthogonal impulse responses to different properties of the cardiac event, these at least two filters each generating a value per time unit corresponding to the morphological resemblance between a portion of the IEGM and the filter impulse response. These values per time unit are supplied to the analyzing unit wherein they are combined and analyzed with respect to the aforementioned defined detection criteria.

With the detector according to the invention a robust functionality in various environments is achieved, which also exhibits improved tolerance towards different modifications of the morphology of the waveform of the considered portion of the IEGM and which requires a simplified signal analysis.

In an embodiment of the detector according to the invention the filter bank is constructed to generate the series of output weight values (not to be confused with the weighting matrix below) from the filters by using previously calculated results in a recursive procedure. Such a recursive implementation is efficient in that it re-uses the result from previous calculations.

In another embodiment of the detector according to the invention the analysis unit calculates the quantity.

$$T(x) = x(n)^T H (H^T H)^{-1} H^T x(n)$$

where $x(n) = [x_{n-m+1}, \ldots x_n]$ denotes the A/D converted IEGM, m the number of samples in $x(n)$, n the current sample at the current time, and H a matrix, determined by the impulse response of the filters. Calculation of the weighting matrix $(H^T H)^{-1}$ does not require an efficient implementation since this is done only once and has no real time constraints.

In yet another embodiment of the detector according to the invention the analysis unit calculates $T(x)$ with a time interval corresponding to k samples where k is an integer, preferably <10. Such a less frequent cardiac event testing will normally be successful since most event peaks exhibit 10–15 samples above the decision threshold. Thus, it is possible to a. o. reduce the energy consumption of the detector by not making a new test for each sample but only for every kth sample. By decreasing the test frequency in this way, only parts of the filter bank calculations need to be performed for each sample, whereas the test, i.e. calculation of the quantity $T(x)$ and comparison with the threshold value γ, is only performed for every kth sample.

In other embodiments of the detector according to the invention the filter bank includes filters with a maximum filter depth, corresponding to a maximum allowed detecting delay. With increasing number of filters the time delay in the longest filter is increasing. In e.g. pacemaker applications a response is normally needed within approximately 40 ms, which consequently limits the maximum filter depth.

In another embodiment of the invention three filters are biphasic and three monophasic. In this way a priori morphologic information about the R-wave has been taken advantage of.

In another embodiment of the detector according to the invention a threshold determining means is provided to determine said threshold from the information about noise level and/or mean (average) peak values of the cardiac event signal. In this way changes in the signal, such as long term morphologic changes and noise level changes can be managed.

The above object also is achieved in accordance with the invention by an implantable heart stimulator, such as a pacemaker, having a detector as described in the above embodiments.

DESCRIPTION OF THE DRAWINGS

FIGS. 6a, 6b and 6c further illustrate the calculations in the filters of the cardiac event detector according to the invention.

FIG. 8 is a simplified flowchart illustrating the adaptive threshold determination in the cardiac event detector according to the invention.

DESCRIPTION OF THE PREFERRED EMBODIMENTS

The kinds of cardiac events, which might be of interest to detect, are e.g. P-, QRS- and/or T-waves. In the following the cardiac event to be detected is merely named "R-wave" for the sake of simplicity instead of writing all different kinds of cardiac events or heart signals that can be processed and detected by the detector according to the invention. The description is based on the embodiment with orthogonal impulse responses.

Figure 1:
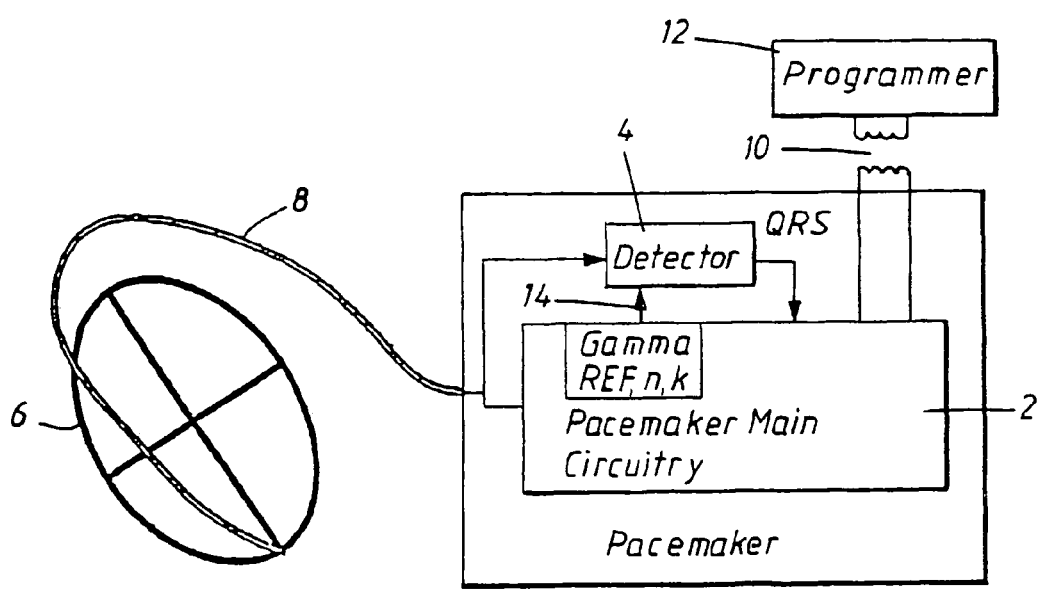
FIG. 1 schematically illustrates the basic components of a pacemaker operable in accordance with the invention.

FIG. 1 is a block diagram showing the main parts of a pacemaker including the detector according to the invention. The block 2 "Pacemaker Main Circuitry" contains all electronic components of a pacemaker according the state of the art. The block 4 "Detector" represents the detector according to the invention. In FIG. 1 the detector 4 has been shown separated from the pacemaker electronic circuitry 2, however, in a practical realization the detector will very likely be included in the pacemaker electronic circuitry.

The pacemaker is connected to the heart 6 of a patient by a lead 8. In the embodiment shown in FIG. 1 the input signals delivered by the lead 8 to the pacemaker and detector are signals from the hearts 6 ventricle or atrium. The pacemaker main circuitry 2 in its turn delivers cardiac stimulation pulses to the lead 8 for transmission to the ventricle or atrium of the heart 6.

The input signals to the detector 4 are signals from the heart 6 transmitted by the lead 8, signals representing information about refractory period of the pacemaker REF, a loop counter signal k to be explained below, signal sample number n and the detection threshold level Gamma, referred to below as γ.

The pacemaker main circuitry 2 also includes a memory for storing data and a wireless communication unit 10 with an external programmer 12. The set of values used for the detection threshold may be stored in these memory means as well.

The signal processing in the detector 4 and the pacemaker main circuitry 2 includes additions, shifts and multiplications of digitized data as will be further described below. Implantable pacemakers of today mostly comprise of a microprocessor, memory and other components necessary for a microprocessor controlled system. This system is normally located in the pacemaker main circuitry 2. The buses 14 for data transfer between the microprocessor system thus located in the pacemaker main circuitry 2 and the detector 4 is not shown in detail in FIG. 1 since the design of such buses are well known to those skilled in the art.

In the detector 4 the heart signals will be A/D converted. The signal processing requires a number of simultaneously existing sequential samples. Therefore memories are needed for storing coexisting signal samples from different times for every calculation performed in the digital signal processing, as will be explained more in detail below. These memories may be formed of the RAM existing in the microprocessor system, but could be memory cells, like shift registers, located inside the detector 4 as well.

An example of the digital signal processing in the detector according to the invention will be described with the aid of the flowchart in FIG. 2. The digitized signals are fed into the bank of matched filters exhibiting symmetric and anti-symmetric impulse responses, cf FIG. 3. The R-wave, or the signal of any other cardiac event to be detected, is modeled by a linear combination of these impulse response waveforms. Symmetric filters are used for modeling monophasic waveforms and anti-symmetric filters for modeling biphasic waveforms. The output signal from the filter bank is subject to further processing in order to obtain the test signal for the detection. This further signal processing can include, e.g. normalization, squaring and summation. The resulting computed quantity is then tested against the detection threshold value Gamma γ, and if the threshold value γ is exceeded a cardiac event is detected.

The implementation of this signal processing is very efficient, since it is performed in a series of steps, wherein the calculation of the next step utilizes the results of the previous steps. This will be further explained below. Furthermore only small integer filter coefficients are used in the filters of the filter bank making the signal processing even more efficient.

Figure 2:
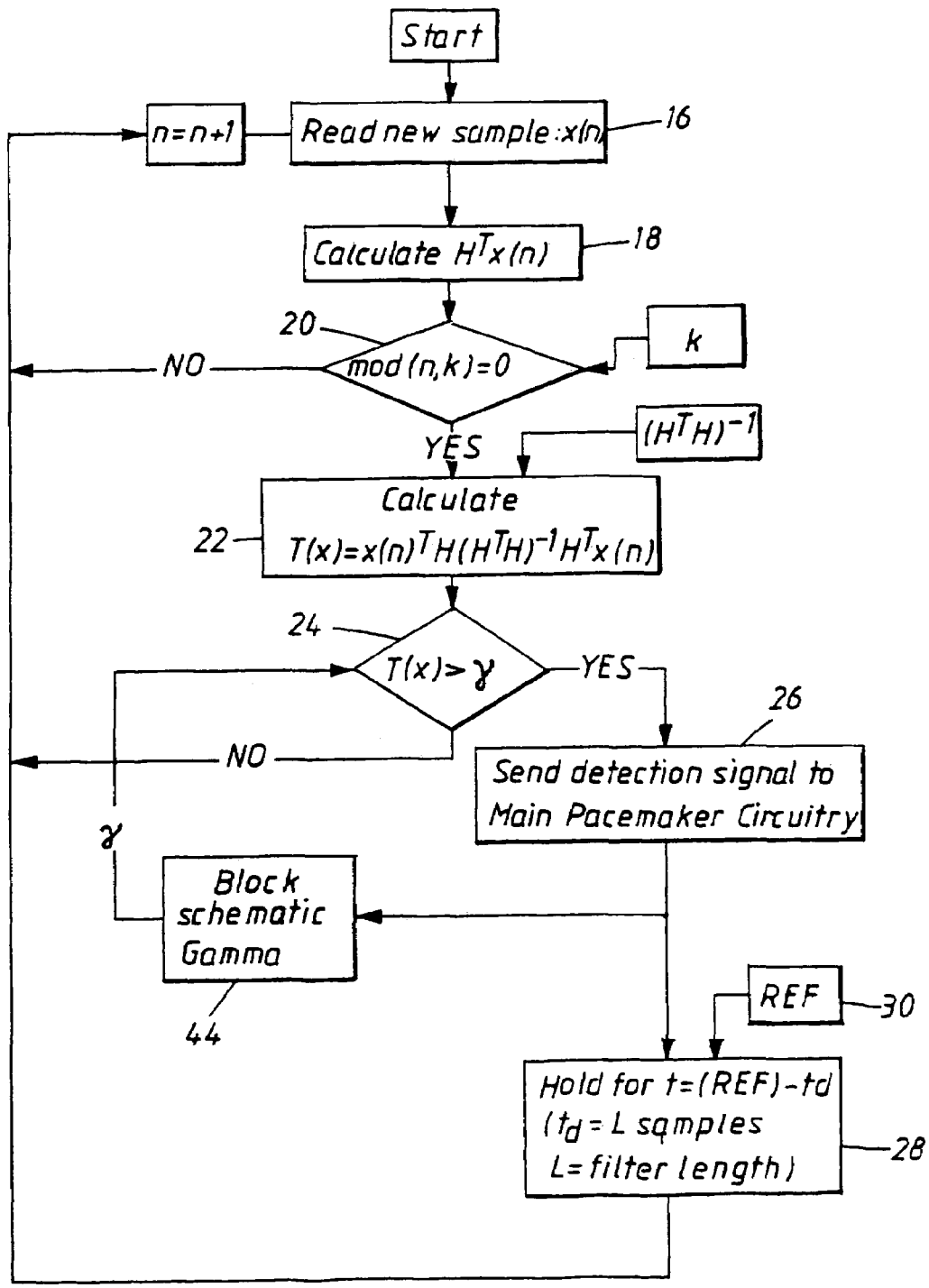
FIG. 2 is a flowchart showing the signal processing that takes place in an embodiment of the cardiac event detector according to the invention.

An example of the digital signal processing in the detector according to the invention is illustrated in FIG. 2. Thus new heart signal samples x(n) are read, at 16 in FIG. 2, and the quantity $H^T x(n)$ is calculated, at 18 in FIG. 2. H denotes a matrix that, as mentioned initially, is determined by the impulse responses of the filters.

The symbol k denotes a predetermined integer determining the frequency of the calculation at 20 in the flowchart, the test frequency, of the quantity T(x), at 22 in the FIG. 2. Thus the quantity T(x) is calculated for each kth signal sample, i.e. with an interval of k samples. The value k is normally less than 10, suitably equal to 5. The expression $H^T x$ is calculated for every sample, but the test frequency, and consequently the frequency for calculating the quantity T(x) is determined by k at 20 as explained above.

If "mod(n, k)=0" at block 20, the input quantity T(x) to the threshold test is calculated by multiplying $H^T X(n)$ with a normalization matrix $(H^T H)^{-1}$ and its transpose $x(n)^T H$. Mathematically this is expressed by the relation in block 22. The detection test is performed by comparing T(x) with the detection threshold level γ. The γ value may be a constant or adaptable to the electrical environment. An adaptive method for determining the threshold will be described below.

If the detection threshold level is not exceeded at the comparison, at block 24 in FIG. 2, a new input signal sample is read and the explained procedure will be repeated. If a detection occurs a signal is sent to the main pacemaker circuitry 2, at block 26 in the flowchart of FIG. 2, carrying the information that a R-wave is present and detected. This information will be used to control the operation of the pacemaker as is well known in the art.

To reduce the power drain the circuits of the detector may be frozen during certain periods of time. This may be the case during the major part of the refractory period. Some time before the end the refractory period, i.e. a number of samples before the end of the refractory period, sampling new input data must be performed. This time or number of samples is equal to the length of the filter L, i.e. equal to the length m of the vector x. Block 28 in FIG. 2 contains a counter for performing this function. The value of the refractory periods REF is separately supplied to block 28, at 30 in the flowchart of FIG. 2.

To further reduce the number of calculations and thereby the power drain, an alternative way of calculating T(x) can be used in the case with filters with orthogonal impulse responses. This simplification is based on rewriting the expression of T(x) by "completing the square". For simplicity it is assumed that only two filters are used, but the methodology can easily be generalized to more filters. Additional simplifications can be made if the filters' impulse responses are orthogonal, since many of the coefficients of $(H^T H)^{-1}$ then are zero. The wanted quantity is $$T(x) = h_{11}^2 \theta_1^2 + h_{12}^2 \theta_1 \theta_2 + h_{21}^2 \theta_2 \theta_1 + h_{22}^2 \theta_2^2$$

However, this expression can also be rewritten as $$T(x) = (h_{11}\theta_1 + h_{22}\theta_2)^2 + (h_{12}^2 + h_{21}^2 - 2h_{11}h_{22})\theta_1\theta_2$$

where $$(H^T H)^{-1} = \begin{bmatrix} h^{11} & h^{12} \\ h_{21} & h_{22} \end{bmatrix}$$

and $$H^T x(n) = [\theta_1 \theta_2]^T$$

which would require fewer calculations.
The equation $$T(x) = x(n)^T H (H^T H)^{-1} H^T X(n)$$

could be written as $$T(x) = x(n)^T H (H^T H)^{-1/2} (H^T H)^{-1/2} H^T x$$

In this expression a vector $$a(x) = (H^T H)^{-1/2} H^T X(n)$$

can be identified. According to this embodiment of the detector the calculated quantity T(x) will be $$T(x) = a(x)^T a(x)$$

A modification which will result in less calculations is to use $$T(x) = a(x)^T \text{sign}(a(x))$$

where sign(a(x)) is a vector of the same length as a(x) but consists of +1 if corresponding elements in a(x)>0 and otherwise equal to −1. This embodiment thus includes a normalizing matrix $(H^T H)^{-1/2}$ and a rectifier. The quantity T'(x) is then used in the following calculations instead of T(x).

Figure 3:
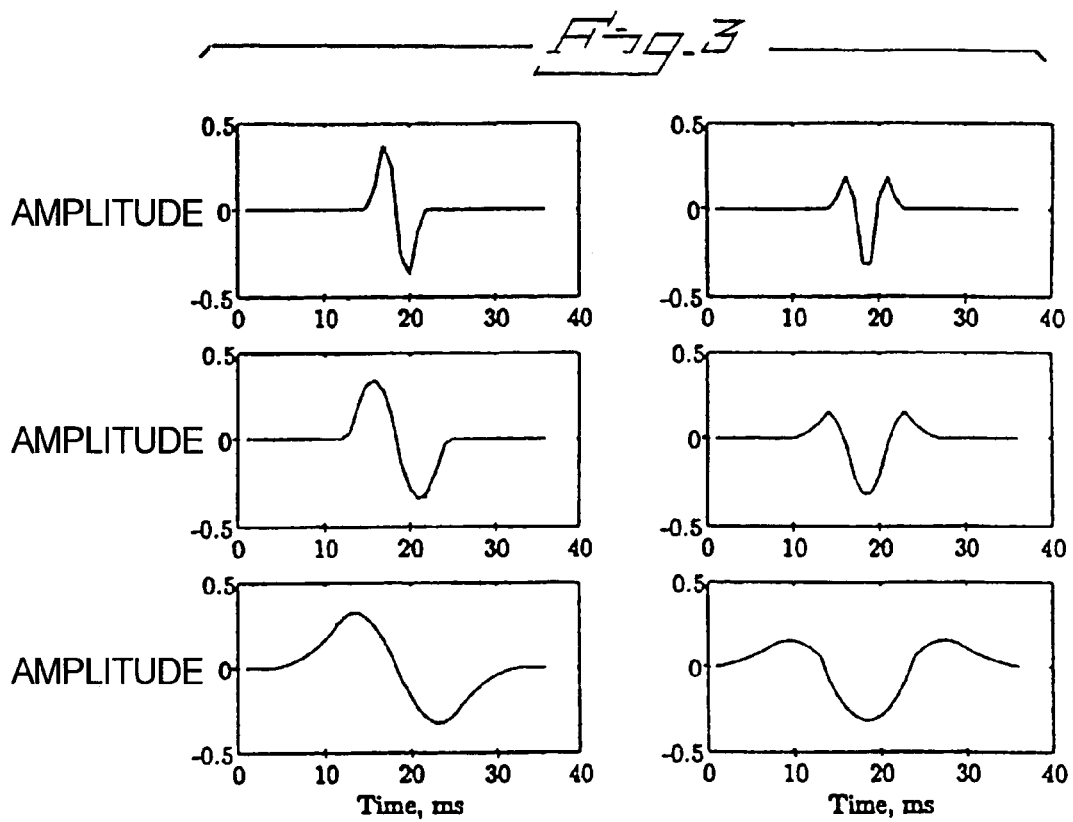
FIG. 3 shows impulse responses for filters in the filter bank in an embodiment of the cardiac event detector according to the invention.

As mentioned above the filter bank of the detector according to the invention comprises a number of filters having symmetric and anti-symmetric impulse response waveforms, see FIG. 3, which shows suitable impulse response waveforms for six filters. These filters have three symmetric and three anti-symmetric waveforms of varying time width for modeling the R-wave as a linear combination of this fundamental waveforms.

After the IEGM has been A/D converted it is thus decomposed into a series of components. If symmetric and anti-symmetric filters of three scales are used as shown in FIG. 3, the composition is obtained by processing the IEGM through six different filters. An important advantage of the detector according to the invention is that in this process use is made of previous calculated results in a recursive way, thereby reducing the number of arithmetic operations.

Figure 4:
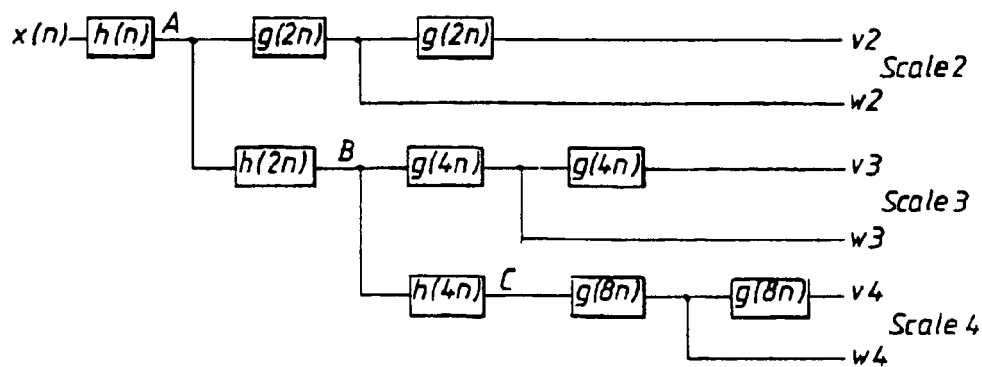
FIG. 4 is a flowchart illustrating the calculation of the filter outputs in the cardiac event detector according to the invention.

FIG. 4 illustrates the digitized signal processing in the filter bank of the detector to calculate the filter outputs.

The A/D converted IEGM samples is denoted by x(n), where n is a number of the current sample. The signal A is the IEGM after processing by the low pass filter h(n). The terms "Scale 2", "Scale 3", relates to the outputs v2 and w2, v3 and w3 . . . respectively As can be seen from FIG. 4 three steps are performed for each scale. The first step is low pass filtering of the incoming signal by h(n). This is performed by passing the signal through a FIR filter defined by the coefficients h(n)=[h1, h2, h3, h4]. The notation h(2n) means inserting zeros between the number in the previous scale, i.e. h(2n)=[h1, 0, h2, 0, h3, 0, h4] and h(4n)=[h1, 0, 0, 0, h2, 0, 0, 0, h3, 0, 0, 0, h4]. h(n) does not necessarily have four elements. This is just an example. In the first level, Scale 2 in FIG. 4 (Scale 1 is not used in this example), signal A is obtained by filtering the IEGM with h(n). The first four samples of the IEGM, x1 . . . x4, is then used to generate the first value of A according the equation $$A(1) = h1*x1 + h2*x2 + h3*x3 + h4*x4$$

In the same way x2 . . . x5 is weighted in order to give $$A(2) = h1*x2 + h2*x3 + h3*x4 + h4*x5.$$

The low pass filter used has preferably the following coefficients $$h(n) = [1, 3, 3, 1]$$

No multiplications are then needed when calculating the convoluted signal. Instead of calculating $$A(1) = x1 + 3*x2 + 3 + x4$$

the fact is used that a signal convoluted three times in series with [1, 1] is equivalent to convoluting it with [1, 3, 3, 1].

The second step is to calculate the output of the anti-symmetric filter. Only the signal values A, and not x, are then used. Of course it would be possible to process the original IEGM with a longer filter, viz representing the impulse response of h(n) convoluted with the impulse response of g(2n), but this would lead to more arithmetic operations.

The filter g(n)=[g1, g2] is a high pass filter. A filter g(n) of two elements is just an example and the filter can contain more elements, cf. e.g. g(2n)=[g1, 0, g2].

If $$g(n)=[-1, 1]$$

no multiplications are needed in this stage either, i.e. the decomposition is obtained solely by additions and subtractions.

To assure that maximum output of all filters occur at the same time during a cardiac event the filter outputs are aligned. This means that all calculations use both previous and "following" values. This does not mean that the filtering is noncausal, i.e. that future values are used, but simply that there is a delay in the system. The delay, however, is not a consequence of the recursive filter output calculation, but depends on the filtering process itself. Taking this into account w2(2) is given by the following equation $$w2(2)=g1*A(1)+g2*A(3)$$

The third and last step is calculation of the output v2 of the symmetric filter. Only values from the anti-symmetric filter w2 is then taken into account, and aligning the outputs gives $$v2(2)=g1*w2(1)+g2*w2(3)$$

When continuing further in FIG. 4, i.e. going to higher scales, signal A is replaced by signal B and C, w2 by w3 and w4, and v2 by v3 and v4. Even more scales can of course be used but for simplicity we assume that only Scales 2–4 are used.

The outputs v3 and v4 as well as w3 and w4 are calculated in the same way as the outputs v2 and w2 with the only difference that the interval between the used samples is larger since g(2n) is replaced by g(4n) or g(8n). Thus for example $$v4(6)=g1*w4(1)+g2*w4(11)$$

whereas $$v2(6)=g1*w2(5)+g2*w2(7)$$

It should also be noticed that $$B(7)=h1*A(4)+h2*A(6)+h3*A(8)+h4*A(10)$$

and $$C(7)=h1*B(1)+h2*B(5)+h3*B(9)+h4*B(13)$$

This is also shown in FIG. 6c.

Figure 5:
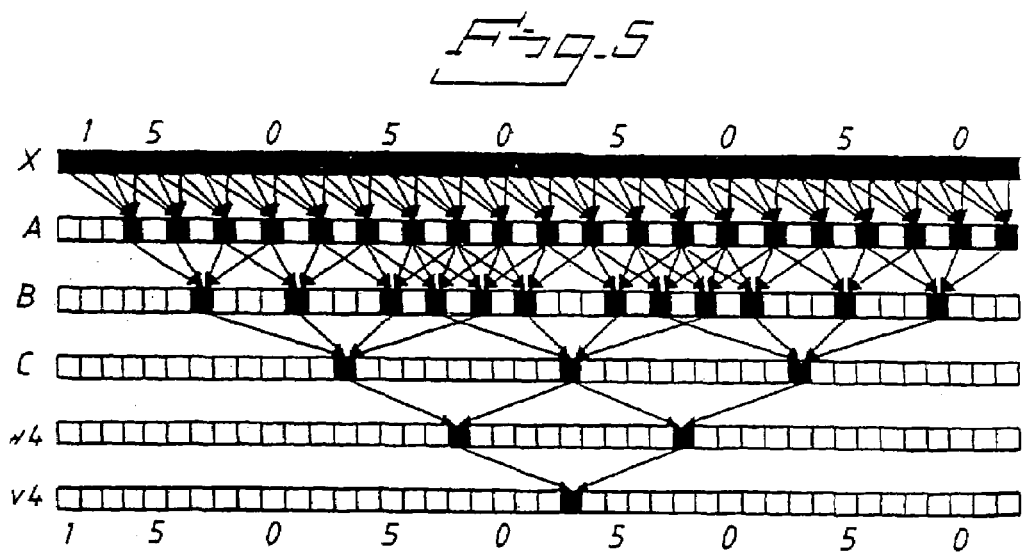
FIG. 5 is a schematic illustration showing how time delays arise in the filter bank of the cardiac event detector according to the invention.
Figure 6A:
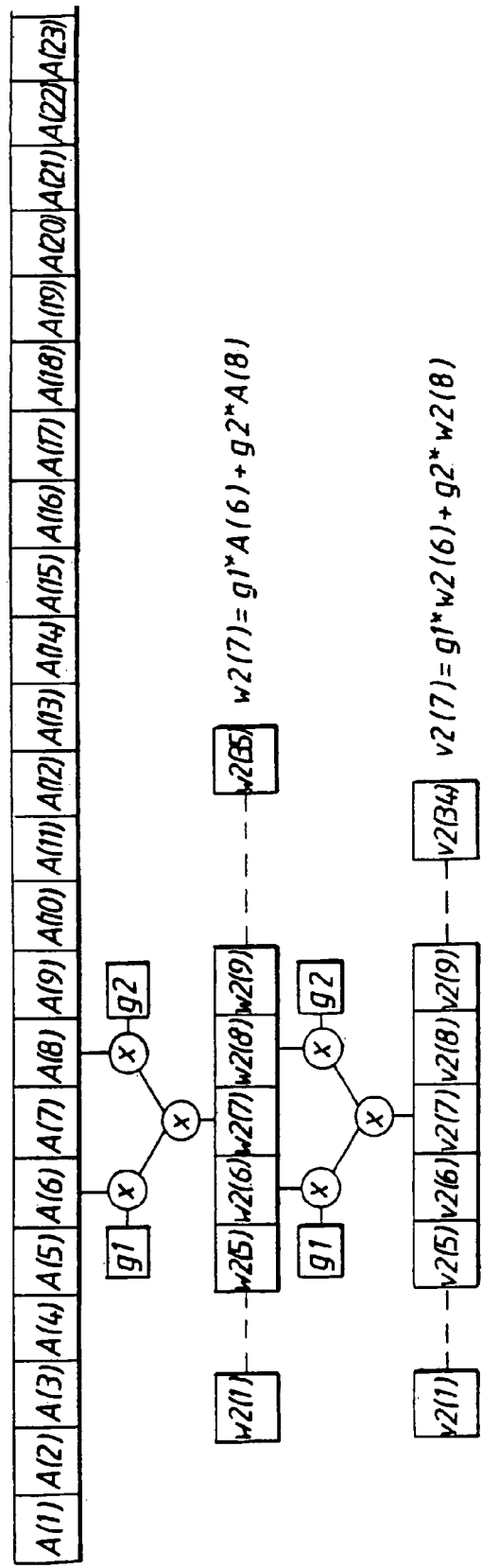

The delay of the filter bank is determined by the largest scale in FIGS. 6a, 6b and 6c since the length of the longest filter determines the delay. This corresponds to $V_{max}$. FIG. 5 illustrates how the delay appears in the system.

The black box at the bottom of FIG. 5 representing v4(23) is calculated using information from w4(18) and w4(28) which in their turn use turn information from the black boxes in array C which are calculated from information in the black boxes in row B in FIG. 5, etc. As can be seen from FIG. 5 the output w4(23) thus depends on the samples x(1) to x(42).

FIGS. 6a, 6b and 6c further illustrate how each component is calculated from previous scales. Just as an example w2(7) is obtained by forming the sum of A(6) and A(8) weighted by g1 and g2 respectively, i.e.

$$w2(7)=g1*A(6)+g2*A(8)$$

The detection threshold level of the detector can be adapted to the actual noise level and the mean value of the peaks originating from the R waves, P waves or whatever cardiac event to be detected. The threshold calculation can be performed after each detection of an R-wave (cardiac event), after a predetermined number of detections or whenever it is assumed that an adaptation on the threshold value is needed.

Figure 7:
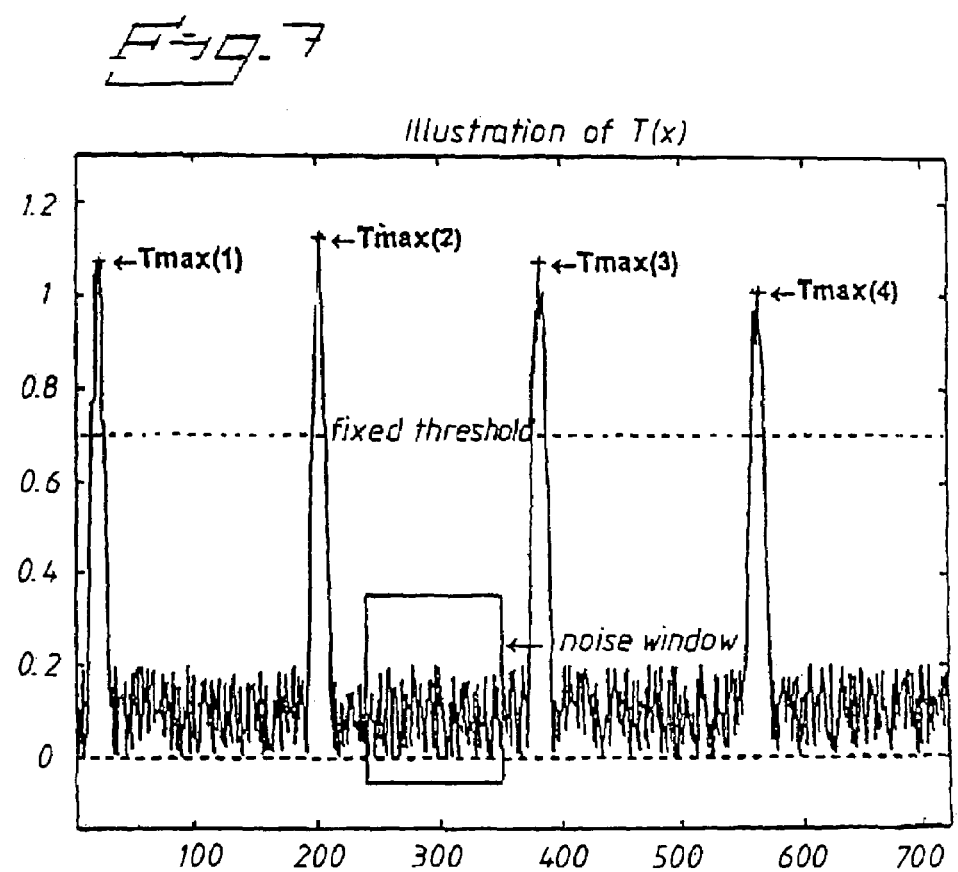
FIG. 7 illustrates the quantity T(x) together with a noise window used for threshold determination in the cardiac event detector according to the invention.

FIG. 7 shows an example of the morphology of the processed signal T(x) with four Tmax values and with a noise window located between two cardiac event detections. In FIG. 7 an example of a fixed threshold value is shown as well.

In case of an adaptive detection threshold, the processed signal T(x) is scanned for determining a peak value. As explained above the detector according to the invention includes a plurality of filters of different lengths. If we suppose that the longest filters includes L IEGM samples, corresponding to approximately 40 ms in a pacemaker application, a peak will probably appear within L/2 samples after the detection. A time window extending from this time to the time of detection is then scanned. The maximum value found within approximately 20 ms after the time of detection is then set as the T(x) peak of the current detection. This maximum value Tmax(i) is stored in a circular buffer storing the last N T(x) peaks, viz. Tmax(i–N+1) to Tmax(i). N may for instance be in the order of 10.

After the peak of T(x) has been determined the noise level is estimated from the processed signal. A noise estimation window, see FIG. 7, extends from a point a predetermined number of samples M after Tmax(i). The values M must be at least equal to L/2, but preferably longer than L/2 in order to exclude data from the T wave, if for instance R-waves are to be detected. The length of the window used to determine the noise level can either be fixed, of the order of 100 ms in case of a pacemaker application, or extend to the next detection. In the later case, the L/2 values prior to the detection must be excluded in order to avoid that the effect of data from the R wave being taken into account. The mean averaging value of some of the T(x) values in the window is calculated and stored as μ(n). Also other characteristic properties of the signal in the time window, for example the signal peak value, can be used as μ(n).

The current threshold is then set to a*γ+(1−a)*μ(n)+η*(μ(T)−μ(n)), where μ(T) is the mean value or other property of the last N Tmax values, η a dimensionless parameter that is fixed or can be set by the programmer, i.e. the physician, and a is a constant between 0 and 1.

FIG. 8 is a flowchart illustrating the adaptive threshold calculation above. Thus in block 32 the peak value index is updated. The T peak value is found and stored in a circular buffer, block 34 in FIG. 8, and in block 36 a new Tmax mean value μ(T) is calculated from the N last Tmax values. In block 38 values from the noise window is stored and the current mean value of T(x) values in the time window is calculated and stored as μ(n), block 40. The new threshold value □ is then set as stated above, block 42 in FIG. 8, where a is a constant between 0 and 1, and this new threshold value γ is supplied to the detector, which is illustrated in the flowchart of FIG. 2 by block 44.

Although modifications and changes may be suggested by those skilled in the art, it is the invention of the inventors to embody within the patent warranted heron all changes and modifications as reasonably and properly come within the scope of their contribution to the art.

The invention claimed is:

1. A cardiac event detector for detecting cardiac events in an IEGM, comprising:
   a plurality of digital filters having respectively different filter characteristics, at least two of said filters having substantially orthogonal impulse responses to different properties of a cardiac event to be detected, said at least two filters each emitting a value per time unit corresponding to a morphological resemblance between a portion of said IEGM and the filter impulse response for that filter; and an analyzing unit supplied with respective outputs from said plurality of digital filters, including said at least two filters, for comparing said output signals with a defined detection criterion for said cardiac event to be detected.

2. A cardiac event detector as claimed in claim 1 wherein each of said at least two filters emits an integer as said value per time unit.

3. A cardiac event detector as claimed in claim 1 wherein said analyzing unit employs the respective values per time unit from said at least two filters as weights for modeling a waveform of said portion of said IEGM in a combination of the respective filter impulse responses.

4. A cardiac event detector as claimed in claim 3 wherein said filters generate said weights using previously calculated weights in a recursive procedure.

5. A cardiac event detector as claimed in claim 1 wherein said analyzing unit performs a mathematical operation on said values for obtaining a mathematical computational result, and compares said mathematical computational result to a predetermined threshold value for determining whether said cardiac event exists.

6. A cardiac event detector as claimed in claim 5 wherein said analyzing unit forms a linear combination of said values as said mathematical computation.

7. A cardiac event detector as claimed in claim 5 wherein said analyzing unit calculates $T(x)=x(n)^T H(H^T H)^{-1} H^T x(n)$, wherein $x(n)=[x_n-m+1, \ldots, x_n]$ representing an analog-to-digital converted IEGM, wherein m designates a number of samples, n designates the current time, H designates a weighting matrix determined from respective impulse responses of said filters.

8. A cardiac event detector as claimed in claim 7 wherein said analyzing unit calculates $T(x)$ with a time interval corresponding to k samples, wherein k is an integer.

9. A cardiac event detector as claimed in claim 8 wherein k is less than 10.

10. A cardiac event detector as claimed in claim 5 wherein said analyzing unit calculates a quantity $T(x)=a(x)^T \text{sign}(a(x))$ wherein $x(n)=[x_n-m+1, \ldots, x_n]$ representing an analog-to-digital converted IEGM, wherein m designates a number of samples, n designates the current time, H designates a weighting matrix determined from respective impulse responses of said filters.

11. A cardiac event detector as claimed in claim 10 wherein said analyzing unit calculates $T(x)$ with a time interval corresponding to k samples, wherein k is an integer.

12. A cardiac event detector as claimed in claim 11 wherein k is less than 10.

13. A cardiac event detector as claimed in claim 1 wherein said filters each have a maximum filter depth corresponding to a maximum permissible detection delay.

14. A cardiac event detector as claimed in claim 1 wherein said filter bank comprises six filters.

15. A cardiac event detector as claimed in claim 1 wherein said filter bank comprises biphasic impulse response filters and monophasic impulse response filters.

16. A cardiac event detector as claimed in claim 15 wherein said filter bank comprises three biphasic impulse response filters and three monophasic impulse response filters.

17. A cardiac event detector as claimed in claim 16 wherein each of said three biphasic impulse response filters respectively comprise fundamental biphasic waveforms with different time extents, and wherein said three monophasic impulse response filters respectively comprise fundamental monophasic waveforms of respectively different time extents.

18. A cardiac event detector as claimed in claim 1 wherein said analyzing unit performs a mathematical operation on said values for obtaining a mathematical computational result, and compares said mathematical computational result to a predetermined threshold value for determining whether said cardiac event exists, and a threshold determining unit for determining said threshold from noise level information.

19. A cardiac event detector as claimed in claim 18 wherein said threshold determining unit determines said threshold based on peak values of said IEGM.

20. A cardiac event detector as claimed in claim 1 wherein said analyzing unit performs a mathematical operation on said values for obtaining a mathematical computational result, and compares said mathematical computational result to a predetermined threshold value for determining whether said cardiac event exists, and a threshold determining unit for determining said threshold anew after each detected cardiac event.

21. A cardiac event detector as claimed in claim 1 wherein said analyzing unit performs a mathematical operation on said values for obtaining a mathematical computational result, and compares said mathematical computational result to a predetermined threshold value for determining whether said cardiac event exists, and a threshold determining unit for determining said threshold anew after a predetermined number of detected cardiac events.

22. A cardiac event detector as claimed in claim 1 wherein said analyzing unit performs a mathematical operation on said values for obtaining a mathematical computational result, and compares said mathematical computational result to a predetermined threshold value for determining whether said cardiac event exists, and a threshold determining unit for determining said threshold anew after a predetermined time period.

23. A heart stimulator comprising:
a pulse generator for generating cardiac stimulation pulses;
a control unit connected to said pulse generator for controlling generation of said stimulation pulses;
an electrode system connected to said pulse generator, and adapted for interaction with a heart, for delivering said stimulation pulses to the heart, and for detecting an IEGM from the heart; and
a cardiac event detector, connected to said electrode system, for detecting cardiac events in an IEGM, comprising a plurality of digital filters having respectively different filter characteristics, at least two of said filters having substantially orthogonal impulse responses to different properties of a cardiac event to be detected, said at least two filters each emitting a value per time unit corresponding to a morphological resemblance between a portion of said IEGM and the filter impulse response for that filter, and an analyzing unit supplied with respective outputs from said plurality of digital filters, including said at least two filters, for comparing said output signals with a defined detection criterion for said cardiac event to be detected, said analyzing unit supplying a result of said analysis to said control unit and said control unit modifying generation of said stimulation pulses dependent thereon.

* * * * *